United States Patent [19]

Acuff et al.

[11] 4,238,196
[45] Dec. 9, 1980

[54] METHODS TO DETERMINE A DIAGNOSTIC INDICATOR OF BLOOD SUGAR CONDITIONS, AND, LIQUID CHROMATOGRAPHIC COLUMNS THEREFOR (CYANIDE FREE)

[75] Inventors: Kenneth J. Acuff, Clinton; Murray A. Rosenthal; Murray E. Volk, both of Akron, all of Ohio

[73] Assignee: Isolab, Inc., Barberton, Ohio

[21] Appl. No.: 90,319

[22] Filed: Nov. 1, 1979

[51] Int. Cl.³ .................... B01D 15/08; G01N 33/16
[52] U.S. Cl. ................................ 23/230 B; 210/656; 210/927; 210/198.2
[58] Field of Search ......... 210/31 C, 198 C, DIG. 23; 23/230 B; 422/70

[56] References Cited

U.S. PATENT DOCUMENTS

| | | | |
|---|---|---|---|
| 4,142,855 | 3/1979 | Acuff | 210/31 C |
| 4,142,856 | 3/1979 | Acuff | 210/31 C |
| 4,142,857 | 3/1979 | Acuff | 210/31 C |
| 4,142,858 | 9/1979 | Acuff | 210/31 C |

Primary Examiner—John Adee
Attorney, Agent, or Firm—Mack D. Cook, II; Paul A. Stux

[57] ABSTRACT

Methods and microcolumns to determine a numerical percentage value as a diagnostic indicator of the blood sugar condition of a specific person. A whole blood sample is lysed and a test sample thereof is placed on a microchromatographic column bed of ion exchange material particles. The column bed is characterized by having no cyanide therein. The column bed comprises an equilibrated suspension of particles selected from the class consisting of CarXH and CarYOH, where "Car" represents an inert substrate for carrying ionizable groups $X^-$ providing dissociated cations $H^+$ and ionizable groups $Y^+$ providing anions $OH^-$. Fractions of various hemoglobin species in the test sample are preferentially eluted or desorbed from the column bed by buffer and wash solutions characterized by having no cyanide therein. Amounts of hemoglobin species in the eluate fractions are detected and measured by spectrometric (color) analysis. A mathematical computation using integer factors corresponding to amounts of various hemoglobin species produces the numerical percentage value.

15 Claims, 1 Drawing Figure

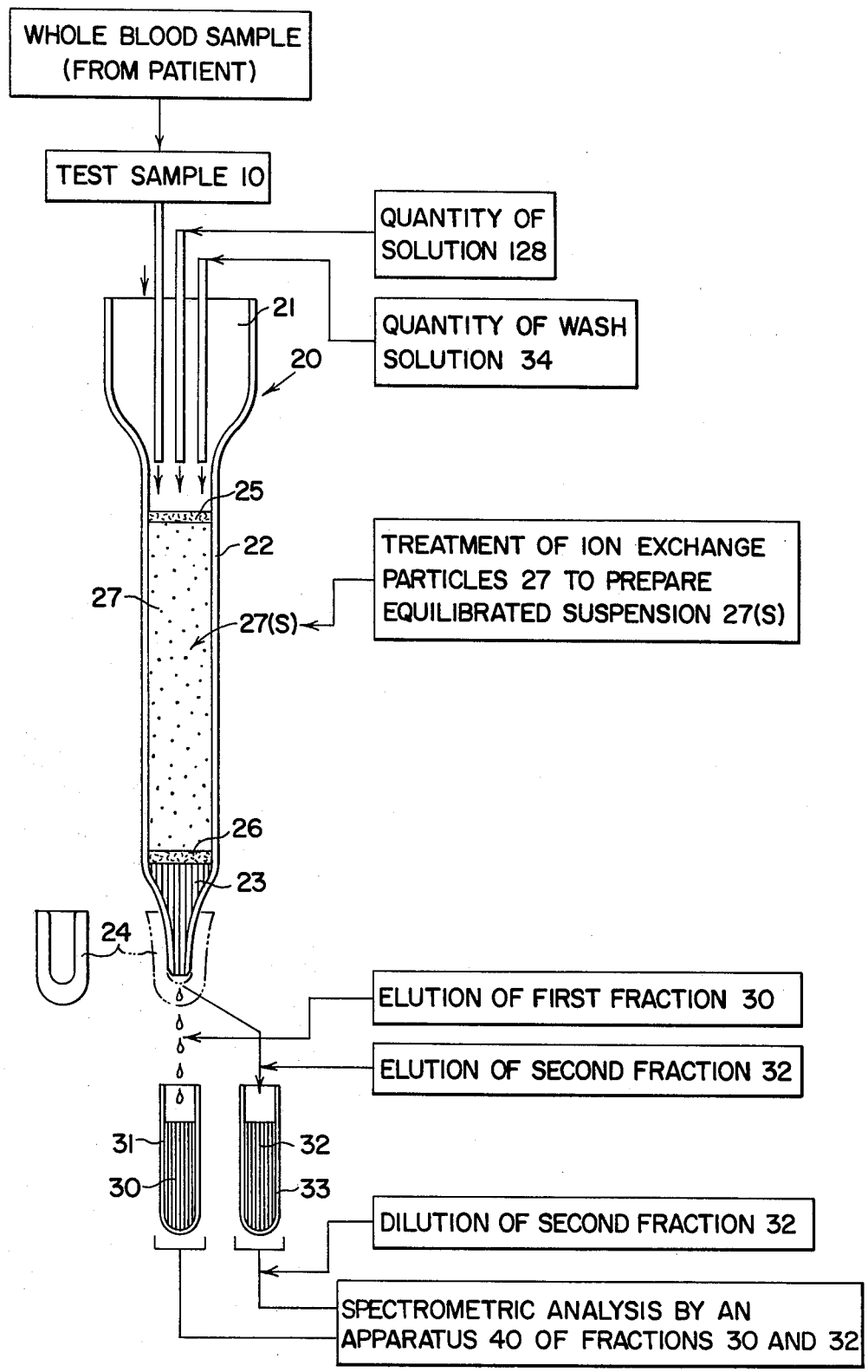

METHODS TO DETERMINE A DIAGNOSTIC INDICATOR OF BLOOD SUGAR CONDITIONS, AND, LIQUID CHROMATOGRAPHIC COLUMNS THEREFOR (CYANIDE FREE)

BACKGROUND OF THE INVENTION

The invention relates to methods to determine a numerical percentage value as a diagnostic indicator of the blood sugar condition of a specific person. The invention also relates to improved liquid chromatographic columns having no cyanide therein for practice of the methods.

According to the invention, a whole blood sample is collected from the person or patient and thereafter prepared as a red blood cell hemolysate test sample using alternative clinical chemistry techniques and procedures. Thereafter, the invention provides a series of steps for separating, detecting and measuring the amount of a group of hemoglobin species present in the test sample using improved ion exchange liquid column microchromatographic apparatus, techniques and procedures, spectrometric analysis, and mathematical computations.

In biochemistry, hemoglobins are the amphoteric protein molecule coloring matter of the red blood corpuscles serving to convey oxygen to the tissues. Several chromatographically separable minor hemoglobins are present in red blood cell hemolysates of normal persons. Some minor hemoglobins are designated as $Hb-A_{1a}$, $Hb-A_{1b}$, $Hb-A_{1c}$, $Hb-A_{1d}$, and $Hb-A_{1e}$. The hemoglobin species $Hb-A_{1c}$ is most prominent and accounts for the major portion of the minor hemoglobins. It is known that the level of hemoglobin $Hb-A_{1c}$ has been related to a patient's average blood sugar level. Normal persons are expected to have 3–6% $Hb-A_{1c}$ relative to their total hemoglobin. Untreated diabetics may have 6–12% $Hb-A_{1c}$ relative to their total hemoglobin, whether the affliction is of the juvenile-onset or adult-onset type. Still further, it is understood that the levels of the species $Hb-A_{1c}$, as a separate and identifiable sub-group, may serve as an indicator of the degree of hyperglycemia, an excess of sugar in the blood, over a prolonged period of time.

The assignee of the present invention, Isolab, Incorporated, is now the owner of five United States Patents relating to methods and columns similar to the methods and columns disclosed herein. These patents are U.S. Pat. No. 4,142,855; No. 4,142,856; No. 4,142,857; and No. 4,142,858, each granted March/1979 to Acuff; and No. 4,168,147, September/1979, also to Acuff.

The first three referenced Isolab-Acuff prior art patents (U.S. Pat. Nos. 4,142,855, 4,142,856 and 4,142,857) use an ion exchange column comprising an equilibrated suspension of cellulose particles. The cellulose particles are of a weak base and anion exchange type in U.S. Pat. No. 4,142,855; of a weak acid and cation exchange type in U.S. Pat. Nos. 4,142,856 and 4,142,857. The last two referenced Isolab-Acuff prior art patents (U.S. Pat. Nos. 4,142,858 and 4,142,147) use an ion exchange column of an equilibrated suspension of resin particles. The resin particles are of a weak acid and cation exchange type.

In each of the Isolab-Acuff patents, reference is made to a "treatment solution" 28 used to prepare the ion exchange particles 27 in the form of an equilibrated suspension 27(S). In each patent, the treatment solution 28, suitably adjusted for pH and/or ionic strength, is also used as the "elution solution" 28 or 128, added to the column 20 after introduction of the test sample 10. Each prior treatment solution 28 and elution solution 28 or 128 has been characterized by the presence of a cyanide compound or anion $CN^-$.

The use of cyanide (KCN) as an ingredient or active compound in buffers or developers for hemoglobin chromatograms has long been accepted as essential; de rigueur. In the prior literature, a paper by Allen et al., Observations on the Chromatographic Heterogeneity of Normal Adult and Fetal Human Hemoglobin: A Study of the Effects of Crystallization and Chromatography on the Heterogeneity and Isoleucine Content, *Journal of the American Chemical Society*, Vol. 80, pp. 1628–1634, April 1958, discloses that "[p]otassium cyanide was originally included in the developers in order to decrease the dissociation of ferrihemoglobin cyanide during chromatography. It was not removed from the developers when oxyhemoglobin was chromatographed because ferrihemoglobin cyanide and oxyhemoglobin have identical chromatographic behavior. Thus, traces of ferrihemoglobin (methemoglobin) in solutions of oxyhemoglobin are converted to ferrihemoglobin cyanide and do not produce slow moving extraneous zones on the column." supra. p. 1630.

Subsequent to the inventions described in the Isolab-Acuff patents, it has been discovered that microchromatographic clinical techniques and procedures to determine an indication or level of the hemoglobin species $Hb-A_{1a-c}$ do not require the presence of a cyanide compound or radical, in either a particle treatment solution or a buffer or elution solution. Indeed, the presence of cyanide may be considered as deleterious.

By way of illustration, each of the Isolab-Acuff patents discloses that the amount of hemoglobin species in a particular eluate fraction, particularly $Hb-A_{1a-c}$, is detected and measured by spectrometric (color) analysis. Each patent specifically discloses that the spectrometric analysis may be performed by an apparatus 40 which measures absorption of light caused by the hemoglobin species present in the test sample 10. The prior patents rely upon the known fact that the visible portion of the spectrum for detecting the presence of a hemoglobin is in the violet range, more specifically, at substantially 415 nm or 4150 Å.

After filing of the applications preceding the Isolab-Acuff patents, it became apparent that the integers expressing the amounts of hemoglobin species present in each eluate fraction (as determined by spectrometric analysis at 415 nm) were affected by a factor of time. When the spectrometric analysis was performed rather promptly (e.g., 30 minutes after elution), the resultant integer would conform to a norm or standard. However, after a longer period of time (e.g., 60 minutes), the resultant integer would reflect a lower value for the hemoglobin species $Hb-A_{1a-c}$. After careful analysis of all aspects of the methods and columns disclosed in the Isolab-Acuff patents, it has now been determined, and is therefore specified as being critical, that the presence of a cyanide compound or radical contributed to an inaccuracy in the true or reasonably correct integer reflecting the hemoglobin species $Hb-A_{1a-c}$ present in a particular and specific test sample.

It is now understood that the presence of cyanide in either the ion exchange particle treatment solution or the buffer solution will increase the incidence of a time-factored conversion of ferrous hemoglobin derivatives to ferrihemoglobin cyanide, with an attendant alteration in the integer or value obtained by spectrometric analysis. Of course, a skilled laboratory person or technician would (and will) compensate for such variation. However, provision of a standard test that can (and will) be performed by relatively unskilled personnel mandates the use of a technique and procedure which does not employ cyanide.

Other advantages of non-use of cyanide will include the facilitation of export-import of microcolumns and reagents according to the invention. In many countries throughout the world, labeling of a product as containing cyanide (even in trace amounts) presents regulatory complications. In countries of product manufacture, elimination of wastes or residue relating to either reagent preparation or ion exchange material equilibration can (and will) give cause to environmental hazard situations and legitimate governmental entity concern. Finally, disposal of used columns and reagent solutions is simplified.

SUMMARY OF THE INVENTION

It is an object of the invention to provide methods to determine a numerical percentage value as a diagnostic indicator of the blood sugar condition of a specific person, without the use of reagents or solutions containing any amounts, trace or otherwise, of any cyanide compound or anion $CN^-$.

It is a further object to provide a method which will separate, detect and measure the ratio of the sub-group of hemoglobin species $Hb-A_{1a-c}$ to the total hemoglobins (Hb) present in the blood of a specific person quickly, inexpensively, accurately and without the presence of a cyanide compound or the anion $CN^-$.

It is still further an object to provide a method which, although requiring of a number of sequential or consecutive steps, is of such a character and nature as to permit the adoption of procedures and protocols which may become standard and routine, permitting persons skilled in the art of clinical chemistry to repeatedly and accurately test the blood of large groups of persons to establish a data base for use by qualified, specialized and medically trained personnel in diagnosing the blood sugar condition of specific persons suspected as being diabetic.

It is still another object of the invention to provide microcolumns, for chromatographic clinical techniques and procedures to determine an indication or level of the hemoglobin species $Hb-A_{1a-c}$, having no cyanide therein but having predetermined microchromatographic characteristics and properties for practice of the methods according to the invention.

These and other objects of the invention, as well as the advantages thereof, will be apparent in view of the detailed descriptions of the various embodiments thereof as set forth below.

In general, the methods according to the invention to determine a numerical percentage value as a diagnostic indicator of the blood sugar condition of a specific person use a whole blood sample taken from such person and thereafter prepared as a test sample containing a red blood cell hemolysate solution. Thereafter, a quantity of the test sample is introduced into an end of a column bed having no cyanide therein which will adsorb hemoglobin species present in said test sample. The column bed comprises an equilibrated suspension of ion exchange material particles having a size less than 100 mesh. The particles in a particular column bed are one member selected from the class consisting of CarXH and CarYOH. "Car" represents an inert substrate for carrying ionizable groups $X^-$ providing dissociated cations $H^+$ and ionizable groups $Y^+$ providing dissociated anions $OH^-$.

It has been determined as critical and essential for the practice of the invention that the CarXH particles be weakly acidic cation exchangers and have a reported $pK_a$: 3–7 and be used in an equilibrated suspension at a pH: 6.0–7.5 at 22.5° C.

It has also been determined as critical and essential for the practice of the invention that the CarYOH particles be weakly basic anion exchangers and have a reported $pK_a$: 7–10 and be used in an equilibrated suspension at a pH: 7.3–9.0 at 22.5° C.

Thereafter, a quantity of a buffer solution having no cyanide therein is introduced into an end of the column bed to preferentially elute therefrom a first fraction which contains certain of the hemoglobin species present in the test sample. When the column bed is an equilibrated suspension of CarXH particles, the first fraction will contain substantially all of the hemoglobin species $Hb-A_{1a-c}$ present in the test sample. When the column bed is an equilibrated suspension of CarYOH particles the first fraction will contain essentially all of the hemoglobin species present in the test sample other than, to the exclusion of, $Hb-A_{1a-c}$. In either event, an aliquot quantity of a first eluate fraction is collected from the other end of the column bed.

In the first method embodiment of the invention, a quantity of a wash solution is introduced into an end of the column bed to desorb and elute therefrom a second fraction which will contain substantially all of the remaining hemoglobin species present in the test sample. When the column bed is an equilibrated suspension of CarXH particles, the second fraction will contain essentially all of the hemoglobin species present in the test sample other than, to the exclusion of, $Hb-A_{1a-c}$. When the column bed is an equilibrated suspension of CarYOH particles, the second fraction will contain substantially all of the hemoglobin species $Hb-A_{1a-c}$ present in the test sample. In either event, an aliquot quantity of a second eluate fraction is collected from the other end of the column bed.

Then, the hemoglobin species present in the first and second eluate fractions are separately detected and measured by spectrometric analysis (color) and the respective amounts thereof are expressed as numerical values which are then compared in accordance with a mathematical formula.

In the second method embodiment of the invention, using a column bed having an equilibrated suspension of either CarXH or CarYOH particles and a buffer solution, an aliquot quantity of a first eluate fraction is collected from an end of the column bed. Also, a quantity of a test sample is significantly diluted to provide a red blood cell hemolysate solution which may be conveniently detected and measured by spectrometric analysis. Then, the hemoglobin species present in the first eluate fraction and in the diluted hemolysate solution are separately detected and measured by spectrometric analysis (color) and the respective amounts thereof are expressed as numerical values which are then compared in accordance with a mathematical formula.

In either method embodiment, an appropriate mathematical formula will provide a numerical percentage value for the hemoglobin species $Hb-A_{1a-c}$ present in a particular test sample for use as a diagnostic indicator of the blood sugar characteristics of the person providing that test sample.

In all embodiments of the invention, the resultant numerical percentage value is available for use by qualified, specialized and medically trained personnel as a diagnostic indicator of the blood sugar characteristics of the patient providing the test sample.

A microcolumn for use in the practice of either embodiment of the invention has a reservoir discharging into a barrel terminating in a discharge tip. The junctures between the reservoir and barrel and the barrel and discharge tip are closed by transverse discs. Ion exchange particles positioned in the barrel between the discs provide a column bed. The discs are permeable to a red blood cell hemolysate solution. The column bed comprises an equilibrated suspension of particles having no cyanide therein. The particles will have a size of less than 100 mesh and in a particular column will have one member selected from the class consisting of CarXH and CarYOH.

THE DRAWING

The drawing schematically shows practice of the invention specifically as to the first method embodiment wherein first and second fractions of hemoglobin species are eluted from an improved chromatographic microcolumn shown substantially in full scale.

DETAILED DESCRIPTION OF THE INVENTION

Practice of the method according to the invention requires the collection of a whole blood sample from a person or patient. The whole blood sample may be taken using conventional clinical chemistry techniques and procedures.

The disclosure of the Isolab-Acuff prior art patents describing in detail two general state of the art procedures for preparing a suitable test sample, referred to generally by the numeral 10, containing a red blood cell hemolysate solution from a whole blood sample, is incorporated herein by reference. A procedure 10-a is used to prepare a test sample 10 which is predominantly the hemoglobin content of the whole blood sample. A procedure 10-b is used to prepare a test sample 10 which may include the plasma proteins, lipids, and the white and red blood cell debris, in addition to the hemoglobin content of the whole blood sample.

With reference to the drawing, which is substantially in full scale, a chromatographic microcolumn is indicated generally by the numeral 20. A column 20 comprises a reservoir 21 discharging into a barrel 22 terminating in a discharge tip 23 selectively closed by a cap 24. The juncture or intersection between the reservoir 21 and the barrel 22 is closed by a transverse plate or disc 25. The juncture between the barrel 22 and the discharge tip 23 is also closed by a transverse plate or disc 26. The ion exchange material particles comprising the column bed between the discs 25 and 26 are referred to generally by the numeral 27.

Each retaining disc 25 and 26 is permeable, having a network of micropores permitting introduction of a red blood cell hemolysate solution from reservoir 21 into the barrel 22, and removal of an eluate fraction from the barrel 22 through the tip 23, while retaining the column bed of particles 27 within the barrel 22. The discs 25 and 26 may be made from a conventional flexible, resilient, linear, high density polyethylene of the Ziegler type. Commercially, this type of filter grade polyethylene is produced and sold under the name Vyon.

According to the invention, the ion exchange material particles 27 have a size less than 100 mesh and are selected from the class consisting of CarXH and CarYOH. "Car" represents an inert substrate and may be cellulosic or a resin copolymer of polystyrene or methacrylic acid and divinylbenzene. $X^-$ represents an ionizable group providing dissociated cations $H^+$ carried by a "Car" and may be a carboxyl group or a carboxymethyl group. $Y^+$ represents an ionizable group providing dissociated anions $OH^-$ carried by a "Car" and may be a diethylaminoethyl group or a mixture of amine groups having the general formulae—$NH_2$, $NHR$ and $N(R)_2$.

The CarXH particles 27 may also be characterized as weakly acidic cation exchangers having a reported $pK_a$: 3-7. The CarYOH particles 27 may also be characterized as weakly basic anion exchangers having a reported $pK_a$: 7-10.

The commercially available form of ion exchange material particles 27 will usually require preparation or treatment for use in a barrel 22 of a microcolumn 20 between the discs 25 and 26. Such treatment could be performed with the particles 27 in situ in the column barrel 22. However, it is preferred that the particles 27 for a series of identical columns 20 be treated using a batch technique, which will permit the use of columns 20 having predetermined microchromatographic characteristics and properties.

The ion exchange material particles 27 constituting the column bed of a column 20 are used in the form of an equilibrated suspension 27(S) having a predetermined or "starting" pH. The CarXH particles are used in a suspension 27(S) at a pH: 6.0–7.5 at 22.5° C. The CarYOH particles are used in a suspension 27(S) at a pH: 7.3–9.0 at 22.5° C. A suspension 27(S) is prepared using a treatment solution 28, having no cyanide therein.

According to the invention, a treatment solution 28 may also be used as buffer solution 128 for elution from a column bed, comprising a suspension 27(S) of either CarXH or CarYOH particles, of an eluate fraction containing certain, but not all, of the hemoglobin species present in the test sample 10.

A quantity of a test sample 10 prepared by either procedure 10-a or 10-b is introduced into one end of a column 20 having a column bed comprising an equilibrated suspension 27(S). A test sample prepared according to procedure 10-a will require a 1:4 dilution using distilled water.

Preferably, the column 20 is positioned vertically, the discharge tip cap 24 is removed and a predetermined volume of a test sample 10 is discharged or placed into the reservoir 21. A major portion of the test sample 10 will pass readily through the disc 25 and onto the column bed of the suspension 27(S). The minor portion of the test sample 10 remaining on or in the disc 25 should be purged or displaced onto the column bed using a small volume (e.g., 0.2 ml) of a solution intended for use as a buffer solution 128 in the next sequential method step according to the invention.

A predetermined or aliquot quantity of a buffer solution 128 having no cyanide therein is discharged into the column reservoir 21 to preferentially elute from the discharge tip 23 a first fraction 30 of the test sample 10. The first fraction 30 is collected in a receiver 31. When the column bed is a suspension 27(S) of CarXH particles, the first fraction 30 will contain substantially all of the hemoglobin species Hb-A$_{1a\text{-}c}$ present in the test sample 10. When the column bed is a suspension 27(S) of CarYOH particles, the first fraction 30 will contain essentially all of the hemoglobin species present in the test sample 10 other than, to the exclusion of, Hb-A$_{1a\text{-}c}$. In either event, after a period of time following addition of the buffer 28, an aliquot quantity of a first fraction 30 will be collected in a receiver 31.

In the first method embodiment of the invention, as shown in the drawing, a second fraction 32 of the test sample 10 is collected in a receiver 33 after an aliquot quantity of a wash solution 34 is discharged into the column reservoir 21. The second fraction 32 will contain substantially all of the remaining hemoglobin species present in the test sample 10. When the column bed is a suspension 27(S) of CarXH particles, the second fraction 32 will contain essentially all of the hemoglobin species present in the test sample 10 other than Hb-A$_{1a\text{-}c}$. When the column bed is a suspension 27(S) of CarYOH particles, the second fraction 32 will contain substantially all of the hemoglobin species Hb-A$_{1a\text{-}c}$ present in the test sample 10. In either event, an aliquot quantity of a second fraction 32 will be collected in a receiver 33.

The wash solution 34 will have no cyanide therein. Otherwise, the precise formula of a wash solution 34 is not critical, so long as use thereof will not alter or modify the spectrometric absorption characteristics ("color") of an eluate fraction 32. A compatible wash solution 34 will have either ionic strength or relative pH sufficient to fully or completely desorb substantially all the remaining blood components of a test sample 10 from a column bed of ion exchange material particles 27. For example, a four milliliter (4 ml) volume of 4 M NaCl may be discharged into a column reservoir 21. After a period of time (e.g., 20–30 minutes), an eluate fraction of substantially 4 ml volume will be collected in a receiver 33. A fraction 32 eluted from a suspension 27(S) of CarXH particles will require of suitable dilution using distilled water prior to the next sequential method step according to the invention.

According to both method embodiments of the invention, the determination of the ratio of Hb-A$_{1a\text{-}c}$ to the total hemoglobins (Hb) present in the whole blood sample collected from the person or patient uses spectrometric apparatus referred to generally by the numeral 40, following performance of liquid column microchromatographic techniques and procedures using a test sample 10.

The spectrometric analysis is performed by an apparatus 40 which measures absorption of light caused by the hemoglobin species present in the test sample 10. It is known that the visible portion of the spectrum for detecting the presence of a hemoglobin is in the violet range, more specifically, at substantially 415 nm or 4150 Å.

The apparatus 40 may be an optical spectrometer "dedicated" or pre-set at the selected wave length of 415 nm. The apparatus 40 may also be a spectrophotometer, a form of spectrometer with associated equipment which supplies the ratio, or a function of the ratio, of the radiant power of two beams as a function of an adjustably selected spectral wave length. Because the spectrometric analysis according to the invention is for the purpose of detecting and measuring hemoglobin species from the test sample 10 by light absorption characteristics, alternative forms of apparatus 40 could be used; for example, visual comparators such as a set of Nessler tubes.

In the first method embodiment of the invention, the contents of the receivers 31 and 33 are individually transferred into appropriate cuvettes for the spectrometric apparatus 40. Spectrometric analysis of the first and second eluate fractions 30 and 32 will provide integers or natural numbers which will express, represent or indicate the amounts of hemoglobin species present in the test sample 10. When using a conventional spectrometer or spectrophotometer as the apparatus 40, the displayed integer is a function of the absorbance (A), a measurement of the amount of light of the spectral wave length of 415 nm absorbed by the hemoglobin species during passage through the cuvette and toward the sensing photocell.

The expressed numerical values for the separately detected and measured hemoglobin species in each eluate fraction 30 and 32 of a particular test sample 10 are then compared in accordance with a mathematical formula.

When the eluate fractions 30 and 32 are eluted from a column bed comprising a suspension 27(S) of CarXH particles, the computation is $$\frac{\text{integer for first fraction } 30 \times 100}{\text{integer for first fraction } 30\ +\ \text{integer for second fraction } 32} = \text{a numerical percentage value.}$$

When the eluate fractions 30 and 32 are eluted from a column bed comprising a suspension 27(S) of CarYOH particles, the computation is $$\frac{\text{integer for second fraction } 32 \times 100}{\text{integer for first fraction } 30\ +\ \text{integer for second fraction } 32} = \text{a numerical percentage value.}$$

In the second embodiment of the invention, using a column bed comprising a suspension 27(S) of either CarXH or CarYOH particles and a buffer solution 128, an aliquot quantity of a first eluate fraction 30 is collected in a receiver 31. Also, either at a prior time, concurrently or consecutively, a quantity of the test sample 10 is prepared as a red blood cell hemolysate solution 42 which may be conveniently detected and measured by spectrometric analysis. It will be apparent that the light absorption characteristics of the test sample 10, without significant dilution, would be of such magnitude as to impair operational efficiency of the sensing photocell of conventional spectrometric apparatus 40. Accordingly, and by way of example, a quantity of test sample 10 equal to the volume of test sample 10 introduced into an end of a column 20, prior to elution of the first fraction 30, should be diluted using distilled water in the ratio substantially 1:480 to prepare a hemolysate solution 42 for analysis by a spectrometric apparatus 40.

The expressed numerical values for the separately detected and measured hemoglobin species in the eluate fraction 30 and in the diluted hemolysate solution 42 of a particular test sample 10 are then compared in accordance with a mathematical formula.

When the eluate fraction 30 is eluted from a column bed comprising a suspension 27(S) of CarXH particles, the computation is $$\frac{\text{integer for eluate fraction 30} \times 100}{\text{integer for hemolysate solution 42}} =$$

a numerical percentage value.

When the eluate fraction 30 is eluted from a column bed comprising a suspension 27(S) of CarYOH particles, the computation is $$100 - \frac{(\text{integer for eluate fraction 30} \times 100)}{(\text{integer for hemolysate solution 42})} =$$

a numerical percentage value.

Use any of these mathematical computations will provide a numerical percentage value for the hemoglobin species Hb-A$_{1a-c}$ present in a particular test sample 10 for use as a diagnostic indicator of the blood sugar characteristics of the person providing that test sample.

The following Examples will further illustrate and describe the practice of the invention by persons skilled in the art of clinical chemistry.

EXAMPLE 1

A CarYOH ion exchange material particle 27 may be of the type wherein "Car" is cellulosic and Y+ is a diethylaminoethyl group, —O—CH$_2$—CH$_2$—N(C$_2$H$_5$)$_2$, having a reported pK$_a$ of substantially 9.5. Commercially, this type of ion exchange material is sold under the name Whatman DEAE-52.

These cellulose particles 27 are prepared as a suspension 27(S) having a pH of substantially 8.5 at 22.5° C. by mixing with a "tris" treatment solution 28 of the formula: 6.06 g H$_2$N.C(CH$_2$OH)$_3$ (0.05 M), with 0.10 g NaN$_3$ (0.01%) as a preservative, made up in one liter of H$_2$O. After mixing with the treatment solution 28, the cellulose particles 27 are then further treated with an acid solution 29 (e.g., 4 M HCl) to readjust to the pH of substantially 8.5.

In both method embodiments of the invention, a quantity of a buffer solution 128 is introduced into an end of a column bed of a suspension 27(S) of these cellulose particles to preferentially elute therefrom an eluate fraction 30 containing essentially all of the hemoglobin species present in a test sample 10 other than Hb-A$_{1a-c}$. The buffer solution 128 may be a "tris" solution of the same formula as the treatment solution 28 with the pH adjusted to substantially 7.7 at 22.5° C. using concentrated HCl.

EXAMPLE 2

Another CarYOH ion exchange material particle 27 may be of the type wherein "Car" is a resin copolymer of polystyrene and divinylbenzene and Y+ is a mixture of primary, secondary and tertiary amine groups having the general formulae —NH$_2$, NHR and N(R)$_2$, where R is an aliphatic hydrocarbon radical such as —CH$_3$ or —C$_2$H$_5$. These particles 27 have a reported pK$_a$:7-9. Commercially, this type of ion exchange material is sold under the names Dowdex MWA-1 and Amberlite IRA-93.

These resin particles 27 may be prepared as a suspension 27(S) having a pH of substantially 7.5 at 22.5° C. by mixing with a "tris" treatment solution 28 of the same formula as in Example 1.

A first fraction 30 of a test sample 10, containing essentially all of the hemoglobin species other than Hb-A$_{1a-c}$, may be eluted from a column bed of a suspension 27(S) of these resin particles by use of a "tris" buffer solution 128 of the same formula as in Example 1, with a pH adjusted to substantially 7.5 at 22.5° C.

EXAMPLE 3

A CarXH ion exchange material particle 27 may be of the type wherein "Car" is a resin copolymer of methacrylic acid and divinylbenzene and X+ is a carboxyl group, —COOH, having a reported pK$_a$:4-6. Commercially, this type of ion exchange material is sold under the name Amberlite CG-50.

The resin polymers 27 are prepared as a suspension 27(S) having a pH of substantially 6.98 at 22.5° C. by mixing with a "phosphate" treatment solution 28 of the formula: 3.74 g KH$_2$PO$_4$ (0.027 M), 0.955 g KOH (0.017 M), with 0.10 g NaN$_3$ (0.01%) as a preservative, made up in one liter of H$_2$O. After mixing with the treatment solution 28, the resin particles 27 are then further treated with an acid solution 29 (e.g., 4 M H$_3$PO$_4$) to readjust to the pH of substantially 6.98.

In both method embodiments of the invention, a quantity of a buffer solution 128 is introduced into an end of a column bed of a suspension 27(S) of these resin particles to preferentially elute therefrom an eluate fraction 30 containing substantially all of the hemoglobin species Hb-A$_{1a-c}$ present in a test sample 10. The buffer solution 128 may be a "phosphate" solution of the same formula as the treatment solution 28 and having a pH of substantially 6.98.

EXAMPLE 4

Another CarXH ion exchange material particle 27 may be of the type wherein "Car" is cellulosic and X− is a carboxymethyl group, —O—CH$_2$—COOH, having a reported pK$_a$ of 3.5. Commercially, this type of ion exchange material is sold under the name Whatman CM-52.

These cellulose particles 27 may be prepared as a suspension 27(S) having a pH of substantially 6.8 at 22.5° C. by mixing with a "phosphate" treatment solution 28 of the formula: 3.74 g KH$_2$PO$_4$ (0.027 M), and 0.748 g KOH (0.013 M), with 0.10 g NaN$_3$ (0.01%) as a preservative, made up in one liter of H$_2$O.

A first fraction 30 of a test sample 10, containing substantially all of the hemoglobin species Hb-A$_{1a-c}$, may be eluted from a column bed of a suspension 27(S) of these cellulose particles by use of a "phosphate" buffer solution 128 of the same formula as the treatment solution 28 and having a pH of substantially 6.8.

EXAMPLE 5

The cellulose particles 27 of Example 4 may be prepared as a suspension 27(S) having a pH of substantially 6.1 at 22.5° C. by mixing with a "bis-tris" treatment solution 28 of the formula: 6.28 g (HOCH$_2$CH$_2$)$_2$ NC(CH$_2$OH)$_3$ (0.03 M), with 0.10 g NaN$_3$ (0.01%) as a preservative, made up in one liter of H$_2$O. After mixing with the treatment solution 28, the cellulose particles 27 are then further treated with an acid solution 29 (e.g., 4 M HCl) to readjust to the pH of substantially 6.1.

A first fraction 30 of a test sample 10, containing substantially all of the hemoglobin species Hb-A$_{1a-c}$, may be eluted from a column bed of a suspension 27(S) of these cellulose particles by the use of a "bis-tris" buffer solution 128 of the same formula as the treatment solution 28 with the addition of 2.34 g NaCl (0.04 M) and having a pH of substantially 6.1.

EXAMPLE 6

The resin particles of Example 3 may be prepared as a suspension 27(S) having a pH of substantially 6.8 at 22.5° C. by mixing with a "bis-tris" treatment solution 28, of the same formula as in Example 5. A first fraction 30 of a test sample 10, containing substantially all of the hemoglobin species Hb-A$_{1a-c}$, may be eluted from a column bed of a suspension 27(S) of these resin particles by the use of a "bis-tris" buffer solution 128 of the same formula as treatment solution 28 with the addition of 7.02 g NaCl (0.12 M), having a pH of substantially 6.8.

SUMMARY

In all embodiments of the invention as described, several steps, techniques or procedures are disclosed wherein dilution, using distilled water, is either required or suggested. It will be understood by a person skilled in the art of clinical chemistry that the best modes of practicing the invention using an improved microcolumn 20 will require careful adoption and consistent following of routine procedures, if the invention is to represent a reliable method of assessing the presence of diabetes and monitoring the degree of diabetic control. It will be further understood by a practitioner of the invention that a procedure or protocol for repetitive testing of large numbers of persons, both diabetic and normal, will inherently incorporate therein: standard quantities and volumes of test samples 10, solutions 28 and 128, 29 and 34, fractions 30 and 32 and solution 42; consistent and compatible dilution ratios; and, careful selection and regulation of the spectrometric apparatus 40. Therefore, the full scope and extent of the invention should be determined solely by the words of the claims appended hereto.

What is claimed is:

1. A method to determine a numerical percentage value as a diagnostic indicator of the blood sugar condition of a specific person, wherein a whole blood sample is taken from said person and thereafter prepared as a test sample containing a red blood cell hemolysate solution, and thereafter, a quantity of said test sample is introduced into an end of a column bed having no cyanide therein which will adsorb hemoglobin species present in said test sample, said column bed comprising an equilibrated suspension of ion exchange material particles having a size less than 100 mesh, said particles in a column bed being one member selected from the class consisting of CarXH and CarYOH, where "Car" represents an inert substrate for carrying ionizable groups $X^{31}$ providing dissociated cations $H^+$ and ionizable groups $Y^+$ providing dissociated anions $OH^-$, said CarXH particles being a weakly acidic cation exchanger having a reported $pK_a$: 3–7 and being used in an equilibrated suspension at a pH: 6.0–7.5 at 22.5° C., said CarYOH particles being a weakly basic anion exchanger having a reported $pK_a$: 7–10 and being used in an equilibrated suspension at a pH: 7.3–9.0 at 22.5° C., and thereafter, a quantity of a buffer solution having no cyanide therein is introduced into an end of said column bed to preferentially elute therefrom a first fraction which contains certain of the hemoglobin species present in said test sample, a column bed which is an equilibrated suspension of CarXH particles providing a said first fraction containing substantially all of the hemoglobin species Hb-A$_{1a-c}$ present in said test sample, a column bed which is an equilibrated suspension of CarYOH particles providing a said first fraction containing essentially all of the hemoglobin species present in said test sample other than Hb-A$_{1a-c}$, and thereafter, an aliquot quantity of said first eluate fraction is collected from the other end of said column bed, and then, a quantity of a wash solution is introduced into an end of said column bed to desorb and elute therefrom a second fraction containing substantially all of the reminaing hemoglobin species present in said test sample, a column bed which is an equilibrated suspension of CarXH particles providing a said second fraction containing essentially all of the hemoglobin species present in said test sample other than Hb-A$_{1a-c}$, a column bed which is an equilibrated suspension of CarYOH particles providing a said second fraction containing substantially all of the hemoglobin species Hb-A$_{1a-c}$ present in said test sample, and then, an aliquot quantity of said second eluate fraction is collected from the other end of said column bed, and then, the hemoglobin species present in the said first and second eluate fractions are separately detected and measured by spectrometric analysis and the respective amounts thereof are expressed as numerical values which are then compared in accordance with a mathematical formula to provide a numerical percentage value for the hemoglobin species Hb-A$_{1a-c}$ in said test sample for use as a diagnostic indicator of the blood sugar characteristics of said specific person.

2. A method to determine a numerical percentage value as a diagnostic indicator of the blood sugar condition of a specific person, wherein a whole blood sample is taken from said person and thereafter prepared as a test sample containing a red blood cell hemolysate solution, and thereafter, a quantity of said test sample is introduced into an end of a column bed having no cyanide therein which will adsorb hemoglobin species present in said test sample, said column bed comprising an equilibrated suspension of ion exchange material particles having a size less than 100 mesh, said particles in a column bed being one member selected from the class consisting of CarXH and CarYOH, where "Car" represents an inert substrate for carrying ionizable groups $X^-$ providing dissociated cations $H^+$ and ionizable groups $Y^+$ providing dissociated anions $OH^-$, said CarXH particles being a weakly acidic cation exchanger having a reported $pK_a$: 3–7 and being used in an equilibrated suspension at a pH: 6.0–7.5 at 22.5° C., said CarYOH particles being a weakly basic anion exchanger having a reported $pK_a$: 7–10 and being used in an equilibrated suspension at a pH: 7.3–9.0 at 22.5° C., and thereafter, a quantity of a buffer solution having no cyanide therein is introduced into an end of said column bed to preferentially elute therefrom a first fraction which contains certain of the hemoglobin species present in said test sample, a column bed which is an equilibrated suspension of CarXH particles providing a said first fraction containing substantially all of the hemoglobin species Hb-A$_{1a-c}$ present in said test sample, a column bed which is an equilibrated suspension of CarYOH particles providing a said first fraction containing essentially all of the hemoglobin species present in said test sample other than Hb-$A_{1a-c}$ and thereafter, an aliquot quantity of said first eluate fraction is collected from the other end of said column bed, and then, a quantity of said test solution is significantly diluted to provide a red blood cell hemolysate solution which may be conveniently detected by spectrometric analysis, and then, the hemoglobin species present in said first eluate fraction and in the said diluted hemolysate solution are separately detected and measured by spectrometric analysis and the respective amounts thereof are expressed as numerical values which are then compared in accordance with a mathematical formula to provide a numerical percentage value for the hemoglobin species Hb-$A_{1a-c}$ in said test sample for use as a diagnostic indicator of the blood sugar characteristics of said specific person.

3. A column bed for use in the method of either claim 1 or 2 comprising a suspension of CarYOH particles at an equilibrated pH of substantially 8.5 at 22.5° C. and wherein "Car" is cellulosic and $Y^+$ is a diethylaminoethyl group.

4. A column bed for use in the method of either claim 1 or 2 comprising a suspension of CarYOH particles at an equilibrated pH of substantially 7.5 at 22.5° C. and wherein "Car" is a resin copolymer of polystyrene and divinylbenzene and $Y^+$ is a mixture of primary, secondary and tertiary amine groups having the general formulae —$NH_2$, NHR, and $N(R)_2$, where R is an aliphatic hydrocarbon radical such as —$CH_3$ or —$C_2H_5$.

5. A column bed for use in the method of either claim 1 or claim 2 comprising a suspension of CarXH particles at an equilibrated pH of substantially 6.98 at 22.5° C. and wherein "Car" is a resin copolymer of methacrylic acid and divinylbenzene and $X^-$ is a carboxyl group.

6. A column bed for use in the method of either claim 1 or claim 2 comprising a suspension of CarXH particles at an equilibrated pH of substantially 6.8 at 22.5° C. and wherein "Car" is cellulosic and $X^-$ is a carboxymethyl group.

7. A column bed for use in the method of either claim 1 or claim 2 comprising a suspension of CarXH particles at an equilibrated pH of substantially 6.1 at 22.5° C. and wherein "Car" is cellulosic and $X^-$ is a carboxymethyl group.

8. A column bed for use in the method of either claim 1 or claim 2 comprising a suspension of CarXH particles at an equilibrated pH of substantially 6.8 at 22.5° C. and wherein "Car" is a resin copolymer of methacrylic acid and divinylbenzene and $X^-$ is a carboxyl group.

9. A microcolumn having no cyanide therein for use in the determination of a numerical percentage value as a diagnostic indicator of the blood sugar condition of a person providing a whole blood sample: having a reservoir discharging into a barrel terminating in a discharge tip, the juncture between said reservoir and said barrel and the juncture between said barrel and said tip each being closed by a transverse disc, said discs being permeable to a red blood cell hemolysate solution test sample prepared from said whole blood sample, and a column bed comprising an equilibrated suspension of ion exchange material particles having a size less than 100 mesh positioned in said barrel between said discs, said particles in a column bed being one member selected from the class consisting of CarXH and CarYOH, where "Car" represents an inert substrate for carrying ionizable groups $X^-$ providing dissociated cations $H^+$ and ionizable groups $Y^+$ providing dissociated anions $OH^-$, said CarXH particles being a weakly acidic cation exchanger having a reported $pK_a$: 3–7 and being used in an equilibrated suspension at a pH: 6.0–7.5 at 22.5° C., said CarYOH particles being a weakly basic anion exchanger having a reported $pK_a$: 7–10 and being used in an equilibrated suspension at a pH: 7.3–9.0 at 22.5° C.

10. A column bed for the microcolumn of claim 9 comprising a suspension of CarYOH particles at an equilibrated pH of substantially 8.5 at 22.5° C. and wherein "Car" is cellulosic and $Y^+$ is a diethylaminoethyl group.

11. A column bed for the microcolumn of claim 9 comprising a suspension of CarYOH particles at an equilibrated pH of substantially 7.5 at 22.5° C. and wherein "Car" is a resin copolymer of polystyrene and divinylbenzene and $Y^+$ is a mixture of primary, secondary and tertiary amine groups having the general formulae —$NH_2$, NHR, and $N(R)_2$, where R is an aliphatic hydrocarbon radical such as —$CH_3$ or —$C_2H_5$.

12. A column bed for the microcolumn of claim 9 comprising a suspension of CarXH particles at an equilibrated pH of substantially 6.98 at 22.5° C. and wherein "Car" is a resin copolymer of methacrylic acid and divinylbenzene and $X^-$ is a carboxyl group.

13. A column bed for the microcolumn of claim 9 comprising a suspension of CarXH particles at an equilibrated pH of substantially 6.8 at 22.5° C. and wherein "Car" is cellulosic and $X^-$ is a carboxymethyl group.

14. A column bed for the microcolumn of claim 9 comprising a suspension of CarXH particles at an equilibrated pH of substantially 6.1 at 22.5° C. and wherein "Car" is cellulosic and $X^-$ is a carboxymethyl group.

15. A column bed for the microcolumn of claim 9 comprising a suspension of CarXH particles at an equilibrated pH of substantially 6.8 at 22.5° C. and wherein "Car" is a resin copolymer of methacrylic acid and divinylbenzene and $X^-$ is a carboxyl group.

* * * * *